(12) United States Patent
Stenzel

(10) Patent No.: US 7,435,256 B2
(45) Date of Patent: Oct. 14, 2008

(54) METHOD AND APPARATUS FOR CONTROLLED DELIVERY OF ACTIVE SUBSTANCE

(75) Inventor: Eric B. Stenzel, Tuam (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 852 days.

(21) Appl. No.: 10/701,455

(22) Filed: Nov. 6, 2003

(65) Prior Publication Data
US 2005/0100582 A1 May 12, 2005

(51) Int. Cl.
A61F 2/06 (2006.01)

(52) U.S. Cl. .................... 623/1.46; 426/423

(58) Field of Classification Search ....... 623/1.42–1.48; 525/415; 426/423
See application file for complete search history.

(56) References Cited

U.S. PATENT DOCUMENTS

| 5,304,121 A | 4/1994 | Sahatjian |
|---|---|---|
| 5,443,458 A | 8/1995 | Eury |
| 5,873,904 A | 2/1999 | Ragheb et al. |
| 5,972,027 A | 10/1999 | Johnson |
| 6,120,536 A | 9/2000 | Ding et al. |
| 6,210,703 B1 | 4/2001 | Novich |
| 6,299,604 B1 | 10/2001 | Ragheb et al. |
| 6,299,905 B1 * | 10/2001 | Peterson et al. ............. 424/486 |
| 6,339,130 B1 * | 1/2002 | Bennett et al. ............. 525/415 |
| 6,368,658 B1 | 4/2002 | Schwarz et al. |
| 6,371,979 B1 | 4/2002 | Beyar et al. |
| 6,395,326 B1 | 5/2002 | Castro et al. |
| 6,468,819 B1 | 10/2002 | Kim et al. |
| 6,805,809 B2 | 10/2004 | Nuzzo et al. |
| 6,849,089 B2 * | 2/2005 | Stoll ........................ 623/1.42 |
| 2001/0027340 A1 | 10/2001 | Wright et al. |
| 2003/0068355 A1 | 4/2003 | Shanley |
| 2003/0149479 A1 | 8/2003 | Snyder et al. |
| 2004/0127976 A1 * | 7/2004 | Diaz ........................ 623/1.42 |
| 2004/0254635 A1 * | 12/2004 | Shanley et al. ............. 623/1.17 |

FOREIGN PATENT DOCUMENTS

| EP | 0 604 022 A1 | 6/1994 |
|---|---|---|
| EP | 0 734 721 A2 | 10/1996 |
| WO | WO 01/15751 A1 | 3/2001 |
| WO | WO 03/030879 A | 4/2003 |
| WO | WO 2004/016298 A | 2/2004 |
| WO | WO 2004/087251 | 10/2004 |

* cited by examiner

*Primary Examiner*—Suzette J Gherbi
(74) *Attorney, Agent, or Firm*—Kenyon & Kenyon LLP

(57) ABSTRACT

The invention relates to a method and device for coating a device with time-release drugs by providing a plurality of micro coated pellets having different release rates on the surface of the medical device structure, e.g., a stent. Organizing the micro pellets with different release rates on the structure can result in the structure having a plurality of release regions with varying release profiles.

20 Claims, 2 Drawing Sheets

METHOD AND APPARATUS FOR CONTROLLED DELIVERY OF ACTIVE SUBSTANCE

TECHNICAL FIELD

The present invention relates to the controlled delivery of therapeutic agents to a target site of an organic vessel.

BACKGROUND

Medical implants are used for a number of medical purposes, including the reinforcement of recently re-enlarged lumens, the replacement of ruptured vessels, and the treatment of disease such as vascular disease by local pharmacotherapy, i.e., delivering therapeutic drug doses to target tissues while minimizing systemic side effects. Such localized delivery of therapeutic agents has been proposed or achieved using medical implants which both support a lumen within a patient's body and place appropriate coatings containing absorbable therapeutic agents at the implant location.

The delivery of expandable stents is a specific example of a medical procedure that involves the deployment of coated implants. Expandable stents are tube-like medical devices, typically made from stainless steel, Tantalum, Platinum or Nitinol alloys, designed to be placed within the inner walls of a lumen within the body of a patient. These stents are typically maneuvered to a desired location within a lumen of the patient's body and then expanded to provide internal support for the lumen. The stents may be self-expanding or, alternatively, may require external forces to expand them, such as by inflating a balloon attached to the distal end of the stent delivery catheter.

Because of the direct contact of the stent with the inner walls of the lumen, stents have been coated with various compounds and therapeutic agents to enhance their effectiveness. These coatings may, among other things, be designed to facilitate the acceptance of the stent into its applied surroundings. Such coatings may also be designed to facilitate the delivery of one or more therapeutic agents to the target site for treating, preventing, or otherwise affecting the course of a disease or tissue or organ dysfunction. The coatings are typically on the order of 3 μm to 100 μm in thickness.

Where a stent is to be coated, care must be taken during its manufacture to ensure the coating is properly applied and firmly adherent to the stent. When the amount of coating is insufficient or is depleted through stripping of poorly adherent coating during manufacture or deployment within the patient's body, the implant's effectiveness may be compromised, and additional risks may be introduced. For example, when the coating of the implant includes a therapeutic, if some of the coating were removed during deployment, the therapeutic may no longer be able to be administered to the target site the desired manner. Similarly, if the therapeutic is ripped from the implant, it can reduce or slow down the blood flowing past it, thereby increasing the threat of thrombosis or, if it becomes dislodged, the risk of embolisms. In certain circumstances, the removal and reinsertion of the stent through a second medical procedure may be required where the coatings have been damaged or are defective.

The mechanical process of applying a coating onto a stent may be accomplished in a variety of ways, including, for example, spraying the coating substance onto the stent, so-called spin-dipping, i.e., dipping a spinning stent into a coating solution to achieve the desired coating, and electrohydrodynamic fluid deposition, i.e., applying an electrical potential difference between a coating fluid and a target to cause the coating fluid to be discharged from the dispensing point and drawn toward the target.

Common to these processes is the need to apply the coating such that the delivery rate can be predictably controlled. For example, in certain applications the goal may be the uniform delivery of the active substance while in other applications the desired effect would be a slow, sustained release of the active substance. Conventional methods include applying the active substance(s) in combination with a polymer to the surface of an implantable device. The drug is released as it elutes through the polymer material when it is placed in the body. One disadvantage of this method is that the polymer material and its composition control the drug's release rate. Another disadvantage is that the polymer provides only one release rate.

For example, the delivery of DNA or therapeutic agent can be inefficient, requiring large amounts of DNA and long delivery times for the stent to be an effective delivery system. This in turn can require large amounts of polymer coating on the stent, adapted to hold and release the DNA over the required period of time. However, if the coating is too thick, expansion of the stent can cause cracking of the coating, thus reducing the effectiveness of the coating. In addition, excessive coating may also cover the open areas in the stent, which normally allow passage of oxygen into the walls of the artery. On the other hand, if the coating is too thin, the entire supply of DNA or the therapeutic agent can be released within a short frame of time.

Controlled drug delivery from medical device coatings is desirable. As described, the conventional technologies rely on bulk release of therapeutic agents from carrier coatings. In this manner, often a rapid burst of the therapeutic agent occurs.

SUMMARY OF THE INVENTION

In one embodiment, the medical device for insertion or implantation in a body includes a structure and at least one therapeutic composition deposited on the structure. The structure can include a first and a second site with therapeutic composition(s) deposited on each site. The therapeutic composition at the first site can be covered with a first protective layer and the therapeutic composition at the second site can be covered with a second protective layer such that the first protective layer provides a faster in vivo decomposition rate relative to the second protective layer, thus enabling the release of the therapeutic composition from the first site at a faster rate than the release rate of the therapeutic composition from the second site.

In another embodiment, each site can have the form of a micro coated pellet (or coated pellets) with each coated pellet including at least one active substance. The active substance can include one or more of the therapeutic agents alone or in combination with excipients and/or placebo. The coated pellets can also include a combination of an active substance with a polymeric composition that covers at least a portion of the active substance. In one embodiment of the invention, each coated pellet can include a micro coating layer substantially covering a core which contains the active substance. In another embodiment, the active substance can be entirely encapsulated by the coating layer. The coated pellets can be similar or dissimilar in composition, size, release rate or decomposition rate.

In yet another embodiment, the invention comprises a stent having deposited thereon a plurality of pellets having one or more coating layers that act as a protective layer. A plurality of coated pellets having a similar release profiles or decomposition rates can be arranged together to form a region. The regions can be discontiguous and/or disconnected. Regions having different release profiles can be positioned linearly along the longitudinal axis of the stent, or as rings around the periphery of the stent, or in any suitable arrangement.

In still another embodiment, the invention comprises a process for preparing a medical device with time-release properties including providing a bio-compatible structure; depositing a therapeutic composition and a protective layer on the structure at a first location and depositing a second therapeutic composition and a protective layer on the structure at a second location. The therapeutic composition and protective layer at the first and the second locations are selected such that the therapeutic composition from the first location is released faster than the therapeutic composition from the second location.

BRIEF DESCRIPTION OF THE DRAWINGS

These and other embodiments of the invention will be better understood with reference to the following exemplary drawings, where.

DETAILED DESCRIPTION

Figure 1:
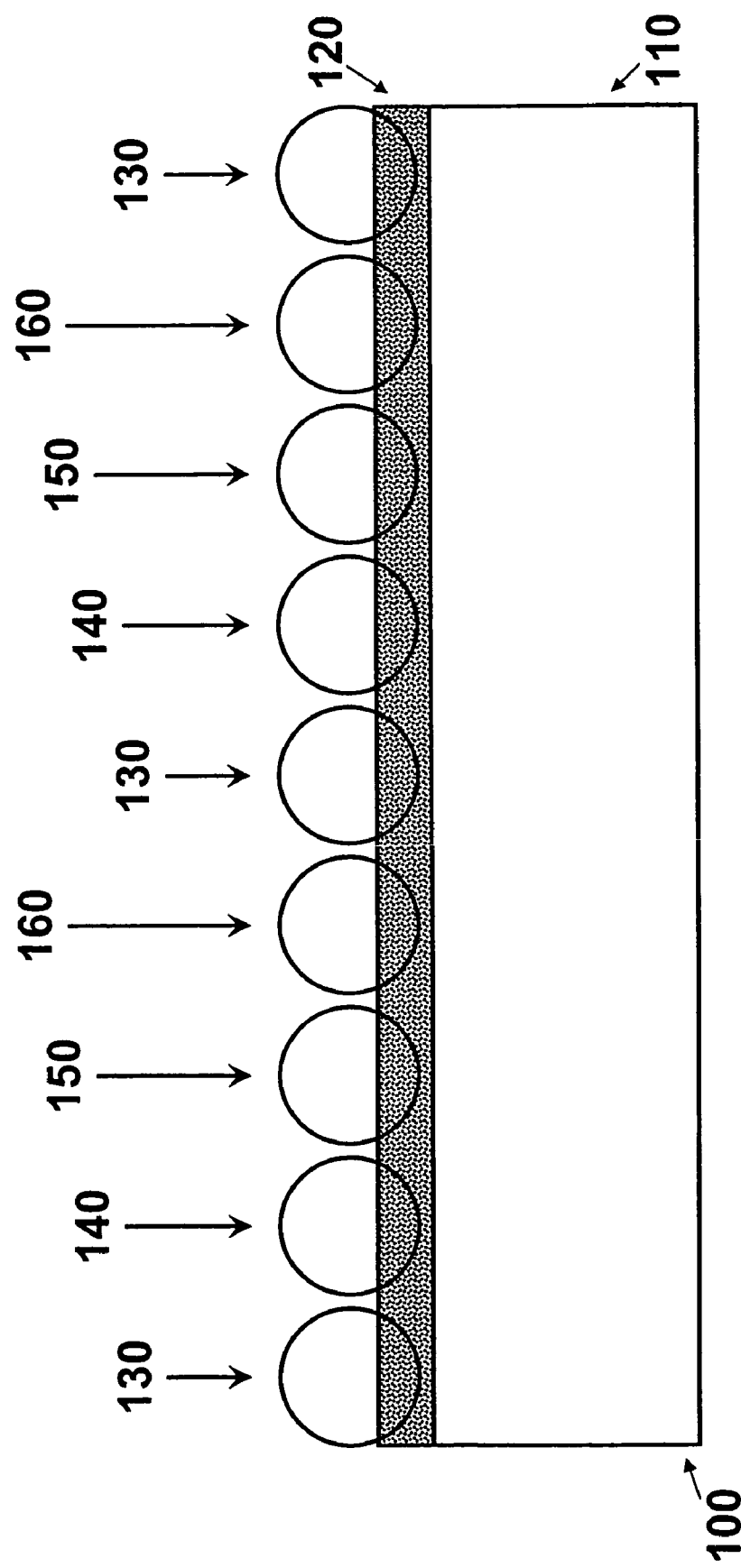
FIG. 1 is a schematic representation of one embodiment of the invention.

FIG. 1 is a schematic representation of one embodiment of the invention. Referring to FIG. 1, an enlarged segment 100 represents a portion of a medical device structure, e.g., a stent strut 110, having deposited thereon an adhesive layer 120. Micro coated pellets 130, 140, 150 and 160 are embedded in adhesive layer 120 and are bonded to stent strut 110. Although not shown, each of the micro coated pellets 130, 140, 150 and 160 is represented as having a different composition and/or dissolution (decomposition) rate.

While the underlying structure 110 represented in FIG. 1 is a stent, it is understood that the invention is not limited thereto. The principles of the invention can be applied equally to any structure adapted for insertion into a body whether the insertion is aimed at permanent or temporary placement of the structure in the body.

Further in reference to FIG. 1, adhesive layer 120 is adapted to receive the micro coated pellets. Adhesive layer 120 can include one or a combination of several bio-compatible polymers (e.g., a polymer matrix). The polymer of the present invention may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference. U.S. Pat. No. 5,091,205 describes medical devices coated with one or more polyisocyanates such that the devices become instantly lubricious when exposed to body fluids. In another preferred embodiment of the invention, the polymer is a copolymer of polylactic acid and polycaprolactone. A preferred polymer can include a tri-block polymer. Exemplary adhesives include cyanoacrylate or fibrin sealants such as TISSEEL® (Baxter Healthcare Corp., Deerfield, Ill.) or Hemaseel® (Haemacure Corp., Sarasota, Fla.).

In one embodiment, adhesive layer 120 comprises a photo-cure polymer that can be activated through exposure to light of a particular wavelength. In another embodiment, adhesive layer 120 comprises a thermally-activated polymer. According to this embodiment, once the micro coated pellets are placed on adhesive layer 120, they can be bonded to the stent strut 110 by heating the substrate and/or the adhesive layer to cure adhesive layer 120. Adhesive layer 120 can be applied by any conventional or known method including, for example, coating, spraying, brushing, contact transfer and electrodynamic coating.

Referring to FIG. 1, micro coated pellets 130, 140, 150 and 160 are arranged side by side as discontiguous parts. The micro coated pellets can be combined to form larger clusters or contiguous sections. Although in the embodiment of FIG. 1, micro coated pellets 130, 140, 150 and 160 are represented as having a spherical shape, the principles of the invention are not limited to this shape and it is contemplated that the pellets, coated or uncoated, can have any shape, form or size. For example, the micro coated pellets may be defined as a region conforming to the shape of the underlying structure.

The micro coated pellets can be arranged according to their expected release profile or decomposition rate. For example, assuming that micro pellets 130, 140, 150 and 160 have different release profiles, they can be arranged on the structure 110 such that micro coated pellets having a substantially similar release profile are not immediately adjacent to each other. In this embodiment, the surface of the structure can be coated to have micro pellets 130 placed along the longitudinal axis of the stent and in a columnar arrangement. With this arrangement, repeating columns of micro coated pellets 130 are adjacent to, for example, columns of micro coated pellets 140 and 160. A similar arrangement can be implemented circumferentially around the periphery of the stent. In this embodiment, repeating rows of micro coated pellets 130 appear as rings around the circumference of the stent. An advantage of this and other similar arrangements is that the coated device has a predictable, and similar release profile throughout its surface. In other words, such an arrangement can predictably release an active substance simultaneously throughout the body of the stent.

Alternatively, the application may demand arranging the micro coated pellets such that the composition(s) at one region, or one end, of the stent would dissolve faster than the composition(s) at other regions. According to this embodiment, it can be predictably said that, for example, the distal end of the stent will begin releasing the active substance long after the proximal end of the stent is depleted.

Because the release profile of a micro coated pellet can be quantified according to the type and the amount of the polymer or biodegradable layer covering the active substance, designers can pre-define a release profile of the medical device by defining the polymer or biodegradable layer and its dissolution characteristics. The amount of the active substance can also be varied according to the desired effect.

In another embodiment, the material covering the active substance can be a porous material that will allow the active substance to leach or elute through the porous openings.

Figure 2:
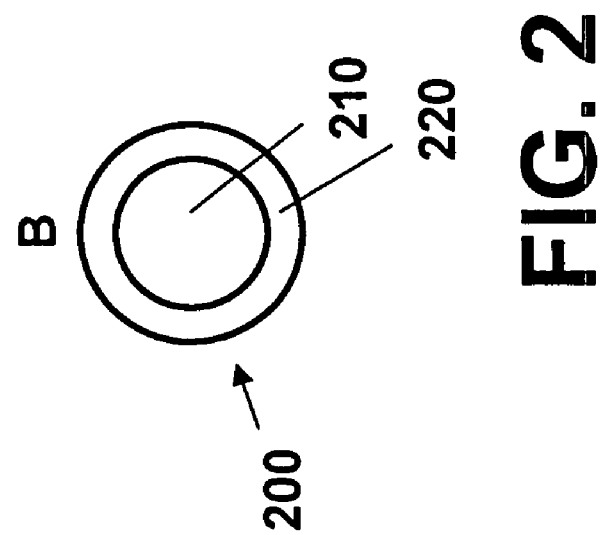
FIG. 2 is a schematic representation of an exemplary micro coated pellet.

FIG. 2 is a schematic representation of an exemplary micro coated pellet. In FIG. 2, micro coated pellet 200 is represented as having core 210 which contains a drug mixture such as an active substance or a mixture of different active substances. In the embodiment of FIG. 2, core 210 is covered with micro coating layer 220. As discussed, micro coating layer 220 can be any polymer or a combination of polymers or other biodegradable material having the desired characteristics. The release profile or decomposition rate of micro coated pellet 200 can be quantified as a function of the physical and chemical characteristics of micro coating layer 220. For example, a micro coating layer 220 made of a polymer that has a very slow dissolution rate (or release rate) in the body would dictate a long release time. Alternatively, a micro coating layer 220 having a relatively fast dissolution rate can be used if a more immediate drug release profile is desired. In addition, the thickness of the micro coating layer 220 can affect the drug release profile. A thicker polymer coating layer would lead to a slower dissolution than a thinner polymer layer of the same composition. Finally, using the same physical characteristics of a micro coated pellet but having different solubility rates can provide a similar drug release rate as that achieved with a thicker coating.

For example, core 210 can be micro coated with a protective biodegradable material that dissolves at a rate of 50% per hour while another core can be micro coated with a protective biodegradable material that dissolves at a rate of 5% per hour. If these two pellets were placed adjacent to each other on a strut, the first pellet having the faster solubility rate will begin to release the drug mixture first. After some time, the polymer coating of the second pellet will dissolve away, and the drug mixture of the second pellet begins to enter the body. Thus, multiple micro coated pellets with different dissolution rates can be placed along a segment of a structure to provide a device with pre-defined time-release characteristics.

In another embodiment, core 210 can include a polymer material mixed with an active ingredient that can elute the active ingredient over a period of time after the micro-coating 210 has partially or completely dissolved. In the exemplary embodiment of FIG. 2, core 210 can be a mixture of 99% polymer compound and 1% drug that elutes over a period of 30 days when micro-coating 220 is partially or completely dissolved. Micro-coating 220 in this example dissolves at a rate of 0.1 μm exposed thickness per day. By varying the thickness of micro-coating layer 220, the beginning of the drug elution core 210 can be delayed as desired to create a micro-pellet with the needed drug release profile.

FIGS. 3A-D are schematic representations of exemplary embodiments of micro coated pellets. In particular, micro coated pellet 300 represented in FIG. 3A includes drug mixture 301 and micro coating layer 302. The drug mixture core can include, for example, an active substance, excipient, placebo or combinations thereof. In the exemplary embodiment of FIG. 3B, active substance 311 is substantially covered by micro coating layer 312. By way of example, FIG. 3A can have 8 μg (25% drug and 75% placebo) of the drug mixture whereas the pellet represented in FIG. 3B can contain 4 μg (50% drug and 50% placebo) of the drug mixture. In addition, micro-coating polymer 302 can be of thickness 0.2 μm and dissolve at a rate of 0.1 μm per day, thus allowing exposure to the therapeutic core 301 up to two days after implantation. Comparatively, micro-coating 312 can have a thickness of 3.0 μm and dissolve at a rate of 0.1 μm per day, thus allowing exposure to the therapeutic core 311 up to thirty days after implantation. In this example, micro coated pellet A would start releasing its content before pellet B starts. There may be a small overlap where both micro coated pellets A and B are releasing simultaneously. Finally, pellet B continues releasing its drug mixture long after pellet A has been completely dissolved.

Figure 3:
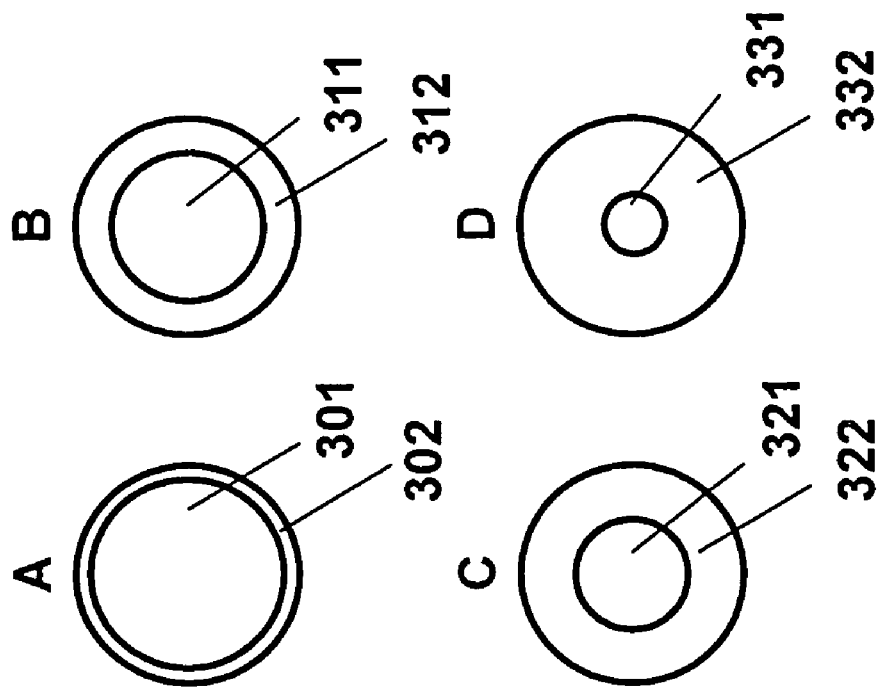
FIGS. 3A-D are schematic representations of exemplary embodiments of micro coated pellets.

As can be seen from FIGS. 3A and 3B, the wall thickness of pellet A is thinner than the wall thickness of pellet B and will dissolve faster in the body, allowing pellet A start releasing the drug before pellet B. In addition, as micro coating 302 dissolves faster than micro coating 312, the supply of the active substance of pellet of FIG. 3A will expire faster than that of FIG. 3B. In the exemplary embodiments of FIGS. 3A and 3B, the pellet represented in FIG. 3A would have a release rate of 0.7 μg/day while the micro coated pellet represented in FIG. 3B would have a release rate of 0.15 μg/day. Since the internal volume of the micro coated pellet represented in FIG. 3A is larger than the micro coated pellet represented in FIG. 3B, the drug mixture of FIG. 3A can contain more placebo in order to ensure that the drug content of the micro coated pellet of FIG. 3A would amount to 2 μg. In this regard, it should be noted that the drug content can also be adjusted to control the release rate.

Referring to FIG. 3C, it can be seen that the wall thickness of micro coating 322 is thicker than the wall thicknesses of micro coatings 302 and 312. As a result, assuming the same composition of coating, micro coating layer 322 will dissolve slower than micro coating layers 302 and 312. Hence the pellet in FIG. 3C starts releasing its contents as pellets of FIGS. 3A and 3B near expiration. The exemplary micro coated pellet of FIG. 3C can contain 2.5 μg of a drug mixture (80% active substance and 20% placebo). The release profile for the micro coated pellet of FIG. 3C can start 10 days after exposure to body fluid and can expire 50 days later.

Referring to FIG. 3D, it can be seen that this micro coated pellet holds the same relationship to the micro coated pellet of FIG. 3C as does the pellet of FIG. 3C to each of the micro coated pellets of FIGS. 3A and 3B. In this exemplary embodiment, the pellet contains 2 μg of drug mixture which is 100% active substance. The micro coated pellet in FIG. 3D starts releasing in 25 days and can expire in 75 days after exposure to body fluid. In the embodiment of FIG. 3C, the pellet would have a release rate of 0.05 μg/day and the micro coated pellet of FIG. 3D would have a release rate of 0.04 μg/day. Furthermore, since the internal volume of the pellet of FIG. 3C is smaller than those of FIG. 3A or 3B, the drug mixture of pellet of FIG. 3C may contain less placebo than each of the pellets 3A or 3B in order to have the drug content be 2 μg, as will the others.

While the exemplary embodiments of FIGS. 3A-3D show that the physical characteristics of the micro coating layer and the drug mixture can be adjusted to obtain a desired release rate, the principles of the invention are not limited thereto. For example, a micro coated pellet can be provided with several alternating layers of drug mixture and polymer micro coating.

In this embodiment, a drug mixture layer can be covered, partially or completely, by a protective polymer layer, which itself is covered by alternating drug layers and protective polymer layers. In this embodiment, the composition of each sublayer and its thickness can be varied to obtain the desired release rate.

In the exemplary embodiment of FIGS. 3A and 3B, the pellet represent in FIG. 3A can have a micro-coating 302 of 0.2 μm thickness that dissolves at a rate of 0.1 μm per day and a core 301 that contains 99% polymer, 0.25% drug and 0.75% placebo which can elute over a period of 30 days. The pellet represented in FIG. 3B can have a micro-coating 312 of 3.0 μm that dissolves at a rate of 0.1 μm per day and a core 311 that contains 99% polymer, 0.5% drug and 0.5% placebo which can elute over a period of 30 days. In still another exemplary embodiments of FIGS. 3A and 3B, the micro-pellet represented by FIG. 3A can begin drug elution two days after implantation and elute therapeutic agent for a thirty-day period where the micro-pellet represented by FIG. 3B would begin drug elution thirty days after implantation and elute therapeutic agent over a thirty-day period.

In this regard, it should be noted that the therapeutic/polymer/placebo mix can be adjusted to control the dosage of elution rate as well as the varying of the micro-coating layer thickness can be adjusted to define the time period before therapeutic elution begins.

The exemplary micro-coated pellet of FIG. 3C can have a micro-coating layer 322 of thickness of 6 μm that dissolves at a rate of 0.1 μm per day and a core 321 containing 99% polymer, 0.75% drug and 0.25% placebo that elutes over a period of 30 days.

The exemplary micro-coated pellet of FIG. 3D can have a micro-coating layer 332 of thickness 9 μm that dissolves at a rate of 0.1 μm per day and a core 331 containing 99% polymer and 1% drug that elutes over a period of 30 days.

In the exemplary embodiment of FIGS. 3C and 3D, the micro-pellet represented by FIG. 3C would begin drug elution 60 days after implantation and elutes therapeutic for a 30 day period where the micro-pellet represented by FIG. 3D would begin drug elution 30 days after implantation and elutes therapeutic over a 90 day period.

The micro coated pellets can be of the same size or can have different sizes depending on the desired release rate and/or the underlying drug composition. To keep the micro coated pellets at substantially the same size, the pellets with the fastest release rate can contain some inert chemical, such as mannitol. If the pellets having the faster release rate are supplied with a thinner micro coating, the addition of an inert compound would serve to increase the volume of the pellet while keeping the drug content constant. In one embodiment of the invention, the pellet size is less than 50 μm.

In a method according to one embodiment of the present invention, a mandrel is placed through an uncoated stent to provide structural support. Then the top surface of the stent (the surface not in contact with the mandrel) is coated with a bio-compatible adhesive layer. The coating process can be done by any number of techniques, including rolling, spraying and roll-to-roll transfer. Once a sufficient amount of adhesive is coated on the stent, micro coated pellets can be imbedded on the stent until all or a portion of the stent is covered. The micro coated pellets can also be supplied to the extent necessary to deliver only the desired amount of the active substance. In one exemplary embodiment of the invention, the micro coated pellets are embedded on the surface of the stent circumferentially as rings with each adjacent ring, line or pellet having a different release rate. Once the micro coated pellets are positioned, the adhesive can be cured to maintain the pellets in place. After curing, the stent can be air brushed to remove the loose pellets. While in this embodiment of the invention, the micro coated pellets are secured to the stent with an adhesive, the principles of the invention are not limited thereto and it is understood that any method for securing the micro pellets to the surface of the stent is deemed to be well within the scope of the invention. For example, the pellets can be sprayed or coated with an adhesive and attached to the device. Alternatively, the pellets can be coated with a material such as a biodegradable wax and placed on the device. Once the pellets and/or the device is heated, the wax melts and adheres the pellets to the surface of the device.

In another embodiment of the invention the micro coated pellets are imbedded on the stent structure by scribing lines (such as aperture, via, bore, groove, cavity, gap or notch) in a blank plate to a set depth and width, filling the scribed lines with micro coated pellets in the desired order, introducing an adhesive or other tacky substance over the stent structure, rolling the stent over the pellet-loaded scribed tray so that the pellets adhere to the stent, substrate and curing the adhesive.

In still another embodiment of the invention, the pellets are arranged on a tacky sheet, the structure is coated with an adhesive tackier than the sheet, and the pellets are transferred to the structure from the sheet after the sheet is imposed and impressed on the structure. Once the tacky sheet is removed and the adhesive on the structure is cured, the pellets will remain embedded on the structure. In an alternative embodiment, the structure is cured with the tacky sheet in place and the sheet is removed after the adhesive on the structure is cured.

In a further embodiment, that adhesive layer can be a polymer material that is mixed with the therapeutic agent that is on the device to form a matrix layer. The matrix layer will elute therapeutic agent over a period of time.

In yet another embodiment, using electrostatic attraction of charged particles (or micro pellets) to a grounded plate, the micro coated pellets are deposited on the end of a flat-tipped blade. The blade is then rolled around the periphery of the stent to make contact around the stent (forming rings) or contacted along the length of the stent from end to end (forming lines). The stent can be optionally coated with an adhesive to receive the micro coated pellets. By cleaning the blade and repeating this procedure for pellets of different composition and/or size, a desired arrangement of micro coated pellets can be obtained.

In another embodiment of the invention, using a precision industrial pick and place system along with a vision system, individual pellets can be placed and imbedded on the desired location of the stent strut. If the stent is pre-coated with adhesive, curing the adhesive would bond the micro coated pellets to its surface.

In still another embodiment, using thin strands of adhesive paper or other tacky strips, thin strips of adhesive can be coated with a range of pellets prior to placing the coated strip in a fixture. Once the fixture is occupied with sufficient number of strands, the stent can be rolled over the strands to effectively transfer the micro coated pellets to the surface of the stent. Alternatively, the strands can be wrapper around the stent. If the stent is provided with an adhesive coating, the coating can be cured to further secure the micro coated pellets thereto.

The term "active substance" and "therapeutic agent" as used herein includes one or more "therapeutic agents" or "drugs". The terms "active substance", "therapeutic agents" and "drugs" are used interchangeably herein and include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences. Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitorfurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

It will be recognized by one of ordinary skill in the art that the embodiments and examples described and illustrated herein are merely illustrative, as numerous other embodiments or permutations thereof may be implemented without departing from the spirit and scope of the present invention.

What is claimed is:
1. A medical device for implantation in a body comprising:
    a structure;
    a set of first coated pellets, each of said first coated pellets containing at least one first therapeutic composition, the set of first coated pellets deposited on the structure at a first site for controlled delivery of the at least one first therapeutic composition to a desired location within the body; and
    a set of second coated pellets, each of said second coated pellets containing at least one second therapeutic composition, the set of second coated pellets deposited on the structure at a second site for controlled delivery of the at least one second therapeutic composition to a desired location within the body;

wherein each of said first coated pellets is covered with a first coating and each of said second coated pellets is covered with a second coating;

wherein the first coating is thinner than the second coating and has a faster in vivo decomposition rate relative to the second coating to release the first therapeutic composition from the first site faster than the second therapeutic composition from the second site; and wherein each of said first coated pellets contains a substance in addition to the first therapeutic composition such that each of the first coated pellets is substantially the same size as each of said second coated pellets.

2. The medical device of claim 1, further comprising an adhesive interposed between the first coated pellets and the structure.

3. The medical device of claim 2, wherein the adhesive layer is one of a polymer, a wax layer, a biodegradable layer or a combination thereof.

4. The medical device of claim 1, wherein one of the first coating or the second coating is one of a polymer, a biodegradable material or a combination thereof.

5. The medical device of claim 1, wherein the medical device is a stent.

6. The medical device of claim 1, wherein one of the first coating or the second coating further comprises a plurality of sublayers.

7. The medical device of claim 1, wherein the first therapeutic composition is the same as the second therapeutic composition.

8. The medical device of claim 1, wherein the first therapeutic composition is different from the second therapeutic composition.

9. A medical device for implantation in a body comprising:
a bio-compatible structure;
a plurality of first coated pellets, wherein each of said first coated pellets comprises a first active substance encapsulated by a first coating; and
a plurality of second coated pellets, wherein each of said second coated pellets comprises a second active substance encapsulated by a second coating thicker than the first coating;
wherein each of said first coated pellets contains a substance in addition to the first active substance and each of said first coated pellets is substantially the same size as each of said second coated pellets.

10. The medical device of claim 9, wherein the first coated pellets have a faster decomposition rate that the second coated pellets.

11. The medical device of claim 10, wherein the second coating on the second coated pellets is thicker than the first coating on the first coated pellets.

12. The medical device of claim 10, wherein the first coating on the first coated pellets has a different composition than the second coating on the second coated pellets.

13. The medical device of claim 9, further comprising a bio-compatible adhesive interposed between the plurality of first and second coated pellets and the structure.

14. The medical device of claim 9, wherein the first active substance is the same as the second active substance.

15. The medical device of claim 9, wherein the first active substance is different from the second active substance.

16. A method for providing a controlled-release of a therapeutic agent from a medical device comprising:
providing a bio-compatible structure;
depositing a set of first pellets comprising a therapeutic composition and a protective layer on the structure at a first location; and
depositing a set of second pellets comprising a therapeutic composition and a protective layer on the structure at a second location;
wherein the therapeutic composition and protective layer at the first location and the second location are selected so that the therapeutic composition from the first location is released faster than the therapeutic composition from the second location;
wherein the protective layer at the first location has a different thickness than the protective layer at the second location; and
wherein said first pellets contain a substance in addition to the therapeutic composition and each of said first and second pellets is substantially the same size.

17. The method of claim 16, further comprising the step of depositing an adhesive layer on the structure prior to the steps of depositing the coated pellets.

18. The method of claim 17, further comprising the step of curing the adhesive.

19. The method of claim 17, further comprising reacting the adhesive layer with therapeutic composition in situ to form a mixture.

20. The method of claim 16, wherein the protective layer at the first location has a different composition than the protective layer at the second location.

* * * * *

UNITED STATES PATENT AND TRADEMARK OFFICE
CERTIFICATE OF CORRECTION

| | | |
|---|---|---|
| PATENT NO. | : 7,435,256 B2 | Page 1 of 1 |
| APPLICATION NO. | : 10/701455 | |
| DATED | : October 14, 2008 | |
| INVENTOR(S) | : Eric B. Stenzel | |

It is certified that error appears in the above-identified patent and that said Letters Patent is hereby corrected as shown below:

Column 1, line 55, "site the" should be changed to --site in the--;
Column 4, line 4, "(BAYHDROL®, etc)" should be changed to --(BAYHYDROL®, etc)--;
Column 4, line 6, "collage" should be changed to --collagen--;
Column 5, lines 54-55, "micro-coating 210" should be changed to --micro-coating 220--;
Column 5, line 65, "pellet 300" should be changed to --pellet--;
Column 7, line 8, "represent" should be changed to --represented--;
Column 8, line 58, "wrapper" should be changed to --wrapped--;
Column 9, line 1, "virus" should be changed to --viruses--;
Column 9, lines 1-2, "andenoassociated virus" should be changed to --adeno-associated virus--;
Column 9, lines 18-19, "viral, liposomes" should be changed to --viral liposomes--;
Column 9, line 43, "nitorfurantoin" should be changed to --nitrofurantoin--;
Column 9, line 45, "lisidomine" should be changed to --linsidomine--;
Column 9, line 51, "Warafin" should be changed to --warfarin--;
Column 9, line 53, "promotors" should be changed to --promoters--;
Column 9, line 55, "promotors" should be changed to --promoters--;
Column 9, line 63, "endogeneus vascoactive" should be changed to --endogenous vasoactive--;
Column 10, line 35, "("BMP's")" should be changed to --("BMPs")--;
Column 10, line 39, "BMP's" should be changed to --BMPs--; and
Column 10, line 45, "DNA's" should be changed to --DNAs--.

Signed and Sealed this

Twenty-second Day of September, 2009

David J. Kappos
*Director of the United States Patent and Trademark Office*